United States Patent [19]

Sickel, deceased

[11] 4,028,492
[45] June 7, 1977

[54] SPEECH AID APPARATUS FOR LARYNGECTOMEES

[75] Inventor: Helmut Sickel, deceased, late of Overath, Germany, by Liesbet Sickel, administrator

[73] Assignee: Dr. Kuhn & Co. GmbH, Cologne (Merheim), Germany

[22] Filed: Feb. 18, 1976

[21] Appl. No.: 659,052

[30] Foreign Application Priority Data

Feb. 22, 1975 Germany .......................... 2507704

[52] U.S. Cl. .............................................. 179/1 AL
[51] Int. Cl.² ........................ A61F 1/20; H04R 9/06
[58] Field of Search ...... 179/1 AL, 107 R, 107 BC, 179/115.5 R, 115.5 PC, 119 R

[56] References Cited

UNITED STATES PATENTS

| | | | |
|---|---|---|---|
| 2,273,078 | 2/1942 | Wright | 179/1 AL |
| 3,072,745 | 1/1963 | Barney | 179/1 AL |
| 3,417,268 | 12/1968 | Lace | 179/115.5 R |

*Primary Examiner*—Kathleen H. Claffy
*Assistant Examiner*—E. S. Kemeny
*Attorney, Agent, or Firm*—Burgess, Dinklage & Sprung

[57] ABSTRACT

In a laryngeal speech aid apparatus comprising a sound head consisting of a clamped hard diaphragm capable of being set in vibration by a plunger, a driver in the form of a vibration coil connected with the plunger and associated fieldwise with a magnet assembly having a permanent magnet, a soft diaphragm connected to the plunger, and a generator-amplifier section connected electrically to the sound head for the production of periodic current pulses for the vibration coil, the improvement wherein (a) the permanent magnet of the magnet assembly consists of a permanent magnetic material designated by the formula $$RECo_5$$

wherein

RE represents one of the rare earth elements

Y, La, Ce, Pr, Nd, Sm or mixtures thereof, and (b) on at least one of sound head and the generator-amplifier section there is provided a rapidly releasable device for the mechanical joining of the sound head and generator-amplifier, as well as a means for maintaining the electrical connection between the sound head and generator-amplifier section when the mechanical coupling is released and the sound head is spatially removed from the generator-amplifier section.

14 Claims, 8 Drawing Figures

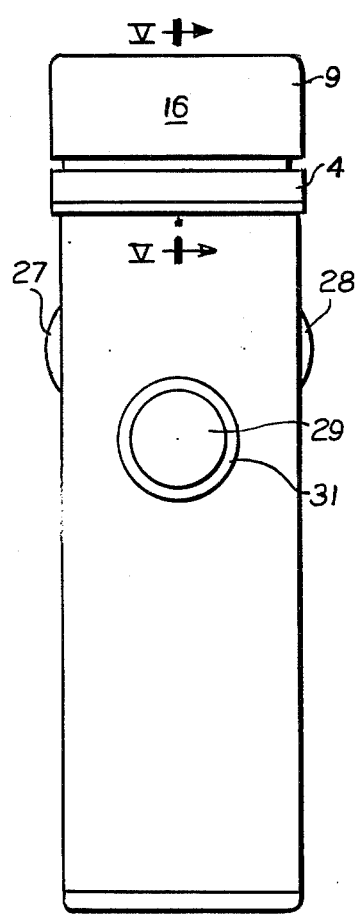
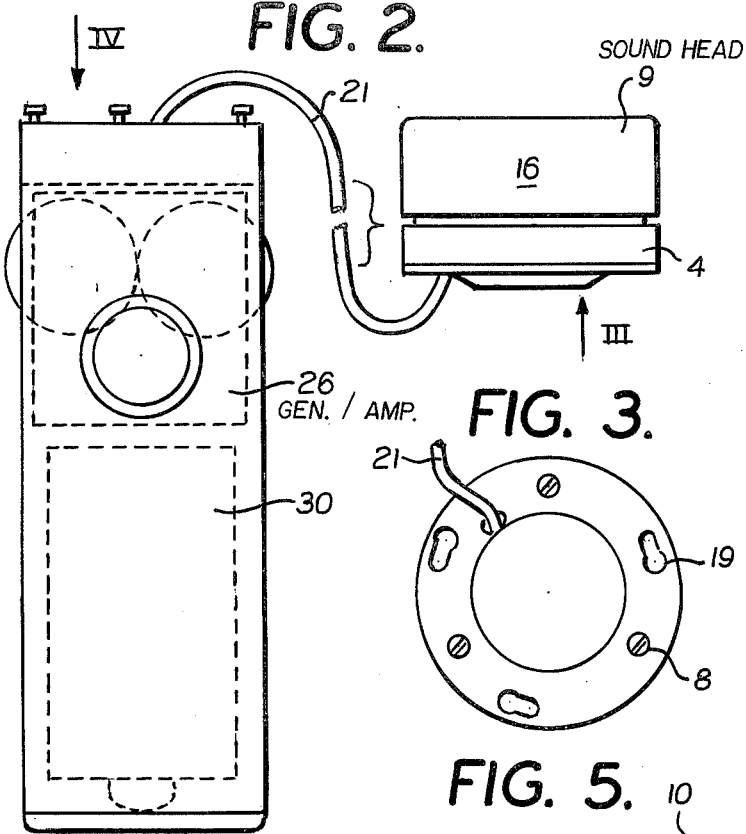
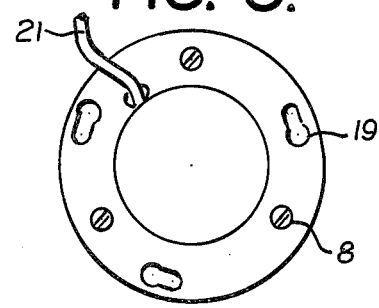
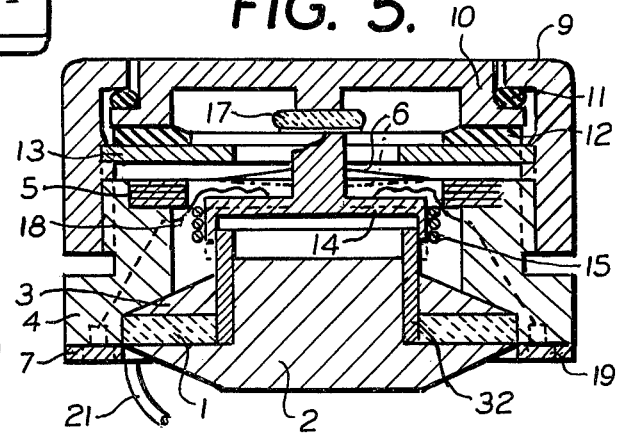
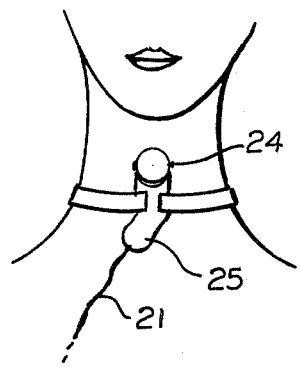
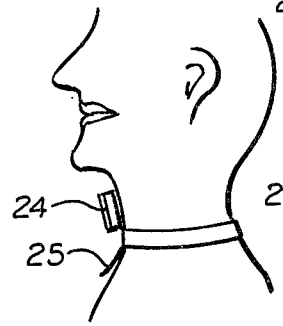
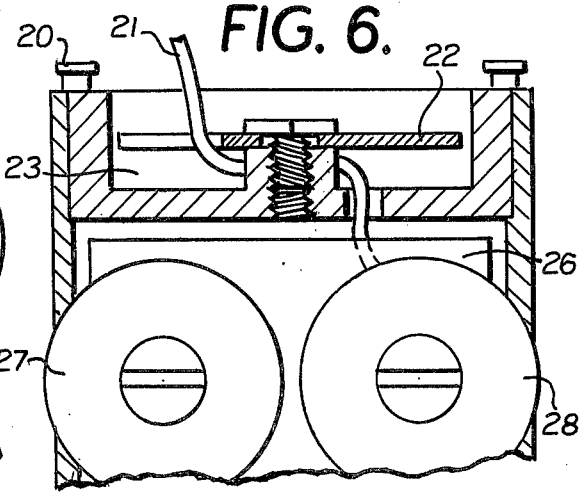

SPEECH AID APPARATUS FOR LARYNGECTOMEES

BACKGROUND

The invention relates to a speech aid apparatus for laryngectomees which has a sound head consisting of a clamped hard diaphragm capable of vibration by a plunger, a driving means in the form of a vibration producing coil joined to the plunger and associated field-wise with a magnet system having a permanent magnet, a soft diaphragm joined to the plunger, and a generator-amplifier joined to the sound head for the production of periodic current pulses for the vibration producing coil. Electronic speech aids of this kind produce a tone which is conducted through the anterior aspect of the neck into the oral-pharyngeal cavity where it can be modulated by movements of the tongue and pharynx to produce intelligible speech. Usually such speech aids permit the frequency and intensity of the tone, and hence the speech, to be adapted to ambient conditions.

In one known speech aid of the initially described type, which resembles a pocket flashlight in construction, the cylindrical handle part contains an audio-frequency generator and amplifier together with potentiometers for regulating the pitch and loudness of the tone, plus a rechargeable battery, while the head part houses the electrodynamic transducer and the plastic hard diaphragm which is clamped between resilient rings. The head and handle form an integral unit which in operation must be applied by hand to the user's throat.

The learning and practice of speech by means of the known speech aid apparatus require extraordinary concentration on the part of the user, both with regard to the coordination of the operation of the amplifier switch with the movements of the mouth and pharynx, and with regard to the point of application and pressure of application of the head portion to the throat. Less practiced users of the known speech aid apparatus, in the effort to concentrate during speech, often find themselves gesticulating unconsciously, so that the head of the speech aid comes partially or completely out of contact with the throat, resulting in failures of voice production in the oral and pharyngeal cavity (cf. "Der Spiegel" news magazine, 1974, Report on Cancer in Germany).

But even for experienced users of the known speech aid, the need to raise to the throat the hand holding the instrument, and the constant occupation of that one hand with speech, is a severe handicap in many activities.

THE INVENTION

The invention, therefore, is addressed to the creation of a speech aid apparatus of the initially described kind, which will be so constructed that, in its operation, an optimum and unvarying contact will be assured between the sound head and the user's throat, and which will nevertheless be usable in a relatively inconspicuous manner. At the same time it is desirable that the new speech aid apparatus be able to be actuated, at least for short periods, in such a manner that both hands will remain free to do other things.

This is accomplished by means of a speech aid apparatus of the initially described kind, which is characterized in that the permanent magnet of the magnet system consists of a permanent supermagnetic material of the $RECo_5$ type (RE representing the rare earth elements yttrium, lanthanum, cerium, praseodymium, neodymium, samarium, or mixtures thereof), and that at least one rapidly releasable fastening means is provided on the sound head and/or on the generator-amplifier for the mechanical joining of the sound head to the generator-amplifier, and also a means for maintaining the electrical connection between the sound head and the generator-amplifier when the mechanical coupling is released and the sound head is located remotely from the generator-amplifier.

The known speech aid apparatus are relatively heavy, their weight being on the order of about 250 grams. The direct mounting of this known, heavy speech aid on the user's throat is therefore impractical, and it is to be noted that the head portion of the instrument is an important factor in the size and weight thereof, especially the construction of its magnetic system. The magnetic system contains a permanent magnet whose field is opposed to the electrical field induced in the electrical coil of the vibrator, and to the magnetic field produced thereby, so as to accelerate the coil and the plunger joined thereto against the hard diaphragm in order to vibrate the latter to produce the tone to replace the human voice.

In the known speech aid apparatus, the permanent magnet forms a relatively large portion of the weight and bulk of the apparatus as a whole, because the materials used hitherto for the permanent magnets of known speech aid apparatus, if the permanent magnet were to be made smaller, would produce too weak a magnetic field to produce tones of sufficient energy to be in any way similar to the human voice. An important reduction of the weight and bulk in comparison with the speech aid instruments currently obtainable has been achieved by the use of a recently developed supermagnetic material having a substantially higher magnetic energy capacity than the present-day conventional materials.

In accordance with the invention, the solution of the problem consists in constructing the speech aid apparatus in two sections, the one being the sound head alone, which is held by an appropriate fastening means in constant and steady contact with the optimum point of application to the throat, while the generator-amplifier, plus the battery if desired, is housed in the other part of the apparatus, which can be carried in some pocket in the user's clothing. Even nervous or temperamental persons can now learn the use of the speech aid apparatus more rapidly and easily, since they no longer have to concentrate on the correct application of the sound head to the laryngeal area of the throat, and all they need do is coordinate the generated tone with the movements of the mouth and pharynx.

The problem of the great weight of the magnet systems of known speech aid apparatus, which would not have permitted the attachment of the sound head alone to the user's throat, is solved by the invention by the use of a material in the permanent magnets which produces a substantially stronger magnetic field than the materials used in the permanent magnets used hitherto in the known speech aid apparatus. This magnetic substance, which is used in accordance with the invention, has substantially higher coercivities and external energies than the magnet material formerly used in the known speech aid apparatus. It consists of intermetallic compounds of the class of the $RECo_5$ magnets (wherein RE represents the following rare earth elements and their mixtures: Y, La, Ce, Pr, Nd, Sm), which are put into the desired shape by powder metallurgical or fusion methods. More information on this new group of materials is to be found in the article, "Kobalt-Seltene Erden: Eine neue Klasse hartmagnetischer Werkstoffe fur Dauermagnete" by Kurt Bachmann, published by Brown Boveri Forschungszentrum, CH-5401 Baden, Switzerland; in a lecture delivered at the "Internationales Symposium uber Eigenschaften elektrisch leitender, magnetischer Materialien" on June 21–22, 1971, in Baden-Baden, Germany. In accordance with the invention, a reduction of the mass of the magnet is achieved in comparison with known speech aid apparatus for the same current pulse produced in the coil and the same electromagnetic force on the coil, so that the sound head in the system of the invention can be made so small that it can be comfortably fastened to the throat without being bothersome to the user due to its weight or to its conspicuousness. By means of the new apparatus it is now possible for laryngectomees to conceal their handicap from persons other than experts, even while they are using the apparatus.

An embodiment of the invention providing a swivel mounting for the sound head affords an especially good means of keeping the sound head in contact with the laryngeal area of the user's throat. This mounting assures a flat contact with the laryngeal area during swallowing, for example, or during movements of the neck.

In the testing of the new magnetic material for the purpose of the invention, it was found that the magnet system designs of known speech aid apparatus are poorly or not at all suitable for the new permanent magnets. The new permanent magnet materials are extremely brittle and fragile. Although the division of the speech aid apparatus into a sound head and a generator-amplifier in accordance with the invention, and the attachment of the sound head to the neck of the user of the apparatus, make the apparatus of the invention less subject to shock than the known hand-held apparatus, the life of the permanent magnet is not satisfactory if it is used in the system of the invention with known magnetic system designs. Consequently, an embodiment which is to be described in connection with FIG. 5 of the appended drawings provides a magnetic assembly in which the permanent magnet is protected on virtually all sides against chipping, and mounts it firmly, yet with a certain resilience, by arranging a sleeve between the yoke rings and the discoidal permanent magnet. At the same time, since the sleeve is then used to guide the coil instead of the gap in the magnet assembly of the prior art, an appreciable saving of material is achieved since the magnet assembly can thus be made shallower. Due to the clamping of the sleeve between the yoke pieces and the discoidal permanent magnet, any slipping or vibrating of these parts against one another is precluded, while at the same time a centering action is achieved.

Additional features of the invention relate to the shape of the parts of the magnet assembly and to the material of which the sleeve between the yoke rings and the discoidal permanent magnet is made. In the latter case the use of plastic offers the additional advantage of a certain resilience in the clamping together of the magnet assembly.

In accordance with another feature of the invention, it is advantageous to mount the magnet assembly within a recess countersunk in the end of the housing such that the magnet assembly will be held by its edges between the shoulder of the said recess and a retaining ring, such that the edge of the fragile permanent magnet will be protected by the housing against chipping and shock. This feature, in conjunction with other features specified above, will provide the permanent magnet with a resilient mounting on all sides.

The means for maintaining the electrical connection between the sound head and the generator-amplifier when they are separated can be a cable fixedly connected at one end to the sound head and at the other to the generator-amplifier, or else the cable can be made removable, in which case internal contact can be provided for the electrical interconnection of the sound head and generator-amplifier when they are locked together. The use of the instrument with the two parts locked together is often convenient when brief conversations are to be conducted by holding the assembled instrument to the throat with the hand in the conventional manner, but when the speech periods are long, the use of the apparatus in the separated mode is of great importance.

The invention thus creates a speech aid apparatus which can be used in two different modes, the changeover from the one mode to the other being accomplished rapidly and easily.

An additional advantage can be achieved by providing in the generator-amplifier section of the apparatus a storage compartment or chamber in which the connecting cable can be stored by means of a cord winding device when the two sections of the apparatus are locked together.

The actuation of the apparatus can be accomplished by operating a switch which is either provided directly on the generator-amplifier or is located elsewhere and connected by conductors to the generator-amplifier. In the latter case it is especially advantageous if the switch is in the form of a pad which can be operated by pressing it with some other part of the body instead of the hand, such as for example the elbow or the upper arm. This would enable the hand corresponding to the actuating arm to remain relatively free for other purposes. It can be especially advantageous to mount the actuating switch in a shallow elastic pocket or the like which can be stitched to the user's clothing in the area of the armpit, so that the speech aid apparatus can be activated by pressing the upper arm against the body and deactivated by lifting the upper arm away from the body.

It is to be noted that, in using the apparatus for speech, the switch must be operated in synchronism with the individual phrases, because the tone produced by the instrument in pauses is bothersome. For this reason, the switch can be an on-off switch, if desired, whether it be mounted directly on the generator-amplifier or separately therefrom, but normally it will be a momentary contact type of switch.

An example of the embodiment of the invention is represented in the drawings, wherein FIG. 1 is a side elevational view of the speech aid apparatus as used when assembled in one unit;

FIG. 2 is a view similar to FIG. 1 showing the apparatus as used when divided into two separate units;

FIG. 3 is a view of the sound head as seen in the direction of the arrow III in FIG. 2;

FIG. 4 is a view of the generator-amplifier section as seen in the direction of arrow IV in FIG. 2;

FIG. 5 is a longitudinal cross-sectional view taken through the center of the sound head, on an enlarged scale;

FIG. 6 is a longitudinal cross-sectional view taken through the center of the upper section of the generator-amplifier;

FIG. 7 is a front view of the sound head attached to the user's throat; and

FIG. 8 is a side view of the sound head attached to the user's throat.

As represented in FIGS. 1 and 2, the speech aid apparatus of the invention consists essentially of a sound head 16 and a generator-amplifier 26, 27, 28. In FIG. 1 the sound head 16 is installed on the generator-amplifier 26, 27, 28, while in FIG. 2 it has been removed therefrom.

Essentially, the generator-amplifier consists of an electronic audio-frequency generator (multivibrator with power amplifier) 26, which is equipped with two potentiometers 27 and 28 for adapting the sound frequency (pitch) and the intensity of the sound (loudness) to the desires of the user of the apparatus. On the generator-amplifier there is additionally provided a switch 29, which can be of the momentary contact type, by means of which the speech aid apparatus can be turned on. The switch 29 is provided with a locking ring 31 whereby it can be secured against unintentional operation, so as to prevent the accidental exhaustion of the rechargeable battery 30 which is provided in the generator-amplifier as the power supply thereof.

The construction and operation of a multivibrator and power amplifier of this kind is generally known and therefore is not further explained herein.

The sound head 16 is shown in greater detail in FIG. 5. It has as its principal parts an approximately cylindrical housing 4 onto which a cap 9 is threaded. By means of the screw cap 9, which has an opening at the top, a hard diaphragm 10 whose top occupies the said opening is resiliently urged against the housing 4. The resilient gripping of the hard diaphragm 10 is accomplished by means of two resilient rings 11 and 12 disposed one on each side of the marginal flange of the hard diaphragm 10. In this manner the hard diaphragm 10 can be drawn tight against a retaining ring 13 by means of the internal margin of screw cap 9, which overlaps its marginal flange, and can be adjusted to the necessary bias tension. The resilient rings 11 and 12 can consist of plastic, preferably plastic foam. The retaining ring 13 in turn is seated on an inwardly extending flange or projection inside of the screw cap 9, and is thus supported against the bias tension.

The hard diaphragm 10 has preferably in its center a boss projecting from its lower side, on which there is placed a pad 17 for engagement by a plunger 14. The pad 17 consists of a material having such properties that the vibrations of the plunger 14 are transmitted in an optimum manner to the hard diaphragm 10 to excite the latter to the desired vibrations.

The plunger 14 is joined to a coil 15 which is guided on a sleeve 32—a plastic sleeve in the present case—the unit consisting of plunger 14 and coil 15 being suspended by a soft diaphragm 6 which is clamped over the end face of the cylindrical housing 4 and thus over the upper aperture thereof. The end face of the cylindrical housing 4 is provided on its inner side with a recess in which a fiber ring is fastened. The fiber ring 5 is fastened in the recess such that its upper side is approximately flush with the end face of the cylindrical housing 4. The soft diaphragm is cemented to the upper side of this fiber ring. The soft diaphragm 6 thus serves as a resilient suspension of the plunger 14 bearing coil 15.

FIG. 5 illustrates in its right-hand and left-hand portions two different positions of plunger 14 bearing coil 15, namely one position slightly below the rest position and another position which is assumed when the coil is energized. When coil 15 is energized, if the polarity of the current is correct, it will be driven upward by the repulsion of its electromagnetic field by the magnetic field of the magnet assembly, thereby accelerating the plunger 14 against the hard diaphragm 10 through the pad 17.

The electric current is delivered to coil 15 through two highly flexible stranded wires 18 connected slackly to the plunger 14, these wires passing through bores in housing 4 and being connected to a cable 21, which will be discussed later on, and which connects the sound head 16 to the generator-amplifier 26, 27, 28.

The construction and the choice of materials in the magnet assembly and permanent magnet have a great influence on the size and weight of the sound head of the apparatus. In the embodiment represented in the drawing, the magnet assembly consists essentially of three parts: an annular permanent magnet 1, a first yoke piece 2 of circular shape whose diameter is approximately equal to the outside diameter of the permanent magnet 1, and which has a boss or core protruding from its center and extending through the rest of the magnet assembly. Furthermore, a second yoke piece 3 of annular shape is provided, which has substantially the same dimensions as the permanent magnet 1. The structure of the magnet assembly is such that the permanent magnet 1 is sandwiched between the two yoke pieces 2 and 3 with the outside edges of all three pieces flush with one another; the openings in the center of the permanent magnet 1 and the second yoke piece 3 are of the same dimensions, so that they form a circular central cavity when assembled, into which the core of the second yoke piece extends, whose diameter is such that an annular gap is left between it and the walls of the central cavity. A sleeve 32 is force-fitted into this annular gap and extends from the bottom of the said gap to a point slightly above the end of the core of the first yoke piece 2. This sleeve holds together the yoke pieces 2 and 3 and the permanent magnet 1 by virtue of the force-fitting, and it centers them and at the same time serves as a guiding means for the coil 15 affixed to the plunger 14.

It is clear, of course, that, although in the embodiment represented in the drawing a circular or annular shape has been selected as the shape of the sound head and especially the magnet assembly, this shape is only a preferred one, and other shapes are entirely conceivable, such as polygonal for example, if they should prove desirable for any reason. Likewise, the term "cylindrical", as used herein with reference to housing 4, must not be interpreted in the narrow sense of the word.

The material of which the permanent magnet 1 in this embodiment consists is a magnetic material of the group of the $RECo_5$ magnets (in which RE represents the rare earth elements Y, La, Ce, Pr, Nd, Sm, and mixtures thereof). On the basis of these intermetallic compounds permanent magnets can be produced having previously unattainable coercive forces and external energies. $SECo_5$ magnets have been made in several laboratories with an external energy $(BH)_{max}$ equal to 20 MGOe (F. F. Westendorp and K. H. J. Buschow: Solid State Commun. 7, 639 (1969); D. K. Das: IEEE Trans. Magn. MAG-5, 214 c1969); D. L. Martin and M. G. Benz: Kobalt 50, 10 C1971). Magnets of this material are being offered on the market with an external energy of 14 to 16 MGOe.

(For information on these materials in general, see the article, "KOBALT - SELTENE ERDEN: Eine neue Klasse hartmagnetischer Werkstoffe fur Dauermagnete" by Kurt Bachmann, published July 1971 by Brown Boveri Forschungszentrum, CH-5401 Baden, Switzerland.)

These new materials for permanent magnets, even as used in the present embodiment, are nevertheless very brittle and fragile. The sandwich method of constructing the magnet assembly, as described above, provides good protection for the permanent magnet against chipping and shock. In the embodiment represented in FIG. 5, this protection is additionally improved by the fact that the outer edge of the magnet assembly is housed within a recess in the lower end of the cylindrical housing 4. As seen in FIG. 5, the configuration of the second yoke piece 3 and that of the seat provided therefor in the housing 4 are matched to one another, a truncoconical configuration being selected for yoke piece 3 for the purpose of saving weight. In the embodiment represented in the drawing, the magnet assembly 1-2-3 is thus securely embedded within the housing 4, the inside diameter of the recess in housing 4 being precisely equal to the outside diameter of the first yoke piece 2, permanent magnet 1 and the second yoke piece 3. The magnet assembly is held in this housing 4 by a ring 7 extending slightly over the outside edge of the first yoke piece 2 and holding the entire magnet assembly in place by means of screws 8 (cf. FIG. 3) threaded into the housing 4.

The housing 4 also is made of plastic in the present embodiment, and the types of plastic used in this housing and in sleeve 32, which is also made of plastic, are selected and adapted to one another such that the permanent magnet 1 will be tightly gripped between the yoke pieces 2 and 3 on the one hand, and on the other hand will be mounted in a resilient and shock-absorbing manner, within certain limits, by the plastic sleeve 32 and the plastic housing 4. In addition, the position of the magnet assembly in relation to housing 4 will be precisely defined, so that the adjustment of the hard diaphragm 10 with respect to the plunger 14 can be effected simply by turning the screw cap 9, and the adjustment will be preserved even when the sound head 16 is removed from the gnerator-amplifier 26-27-28.

A connecting cable 21 provides the electrical connection between the sound head 16 and the generator-amplifier 26-27-28. The connecting cable 21 is anchored at one end to the sound head 16 and at the other to the generator-amplifier 26-27-28.

The means for the mechanical joining of the sound head to the generator-amplifier is in the form of screws 20, in the present embodiment, which are provided on the generator-amplifier 26-27-28 (FIG. 6) and form, together with the keyhole-shaped apertures 19 in the ring 7 on the sound head 16 (FIGS. 3 and 5), a kind of bayonet lock which can be rapidly released or relocked by a slight rotation.

To house the electrical cable 21 when the sound head 16 is attached to the generator-amplifier 26-27-28, a chamber 23 is provided in the upper section of the generator-amplifier (FIG. 6), and contains a winding disk 22 by means of which the cable 21 can be wound up and stowed away in the storage chamber 23. Once the cable is wound up in the storage chamber 23, the sound head 16 can be attached to the generator-amplifier, resulting in the assembly as illustrated in FIG. 1. In this state, which may be desirable for use in brief conversations, the apparatus would normally be carried about.

To use the new speech aid apparatus in its separated mode (FIGS. 2 to 4 and 7 and 8), the sound head 16 is removed from the generator-amplifier by rotating it slightly, then the connecting cable 21 is unwound from the storage chamber 23, and the sound head 16 is attached to a mounting 24 which is on a support 25 fastened to a neckband, for example. In the embodiment represented, the mounting 24 on the support 25 is a swivel mounting such that the sound head can turn in all directions. The support 25 can be attached to the neckband in any desired manner—for example, by means of a dual slit, as shown in FIG. 7. The generator-amplifier section 26-27-28 is then placed in the user's clothing at some suitable location.

In the drawing in FIGS. 1 and 2, the switch 29 is mounted on the generator-amplifier 26-27-28. However, it may also be separate from the generator-amplifier and be connected thereto electrically. If it is separate, it can also be located at some point in the user's clothing where it will be easy to operate with the hand, while the generator-amplifier will be carried where its weight will cause the least disturbance.

When the switch 29 is separate from the generator-amplifier, it can be still more advantageously in the form of a shallow element having a large actuating surface area. Either the switch or sensing device itself may be shallow, or it can be contained in a shallow, resilient housing whose cover has a certain stiffness and resilience. It will then be possible to place the switch at such points of the body as the armpit, for example, at which it can be operated by parts of the body other than the hand, such as the upper arm of the user of the speech aid, for example, which can be pressed against the upper body, or the elbow which can be pressed against the waist; in the latter case the switch means, in the form of a shallow element, would have to be located on the user's side, at the waistline.

Not shown in the drawing is still another embodiment of the means for the mechanical and electrical connection of the sound head 16 to the generator-amplifier 26-27-28. In this embodiment, the electrical connection between the sound head and the generator-amplifier is accomplished by direct contact between the first yoke piece 2 and a spring contact situated in the upper part of the generator-amplifier 26-27-28, on the one hand, and between the keyhole-shaped apertures 19 and the screws 20 on the other. In this embodiment of the invention it is necessary that the housing 4 be made of plastic and that the ring 7 containing the keyhole-shaped apertures 19 be electrically insulated from the first yoke piece 2.

This embodiment has the advantage that, in the assembled state, i.e., in the unseparated mode of operation of the speech aid apparatus, no cable such as cable 21 in the embodiment described above is necessary. When the speech aid apparatus is used in two separate parts, the electrical connection of the sound head 16 to the generator-amplifier 26-27-28 is effected by means of an adapter cable which is attached at one end to the mount provided for the sound head on the neckband, and at the other end can be plugged into a socket provided on the generator-amplifier 26-27-28.

It will be understood that the specification and examples are illustrative but not limitative of the present invention and that other embodiments within the spirit and scope of the invention will suggest themselves to those skilled in the art.

What is claimed is:

1. Speech aid apparatus for laryngectomees, comprising a sound head consisting of a clamped hard diaphragm capable of being set in vibration by a plunger, a driver in the form of a vibration coil connected with the plunger and associated field-wise with a magnet assembly having a permanent magnet, a soft diaphragm connected to the plunger and a generator-amplifier section connected electrically to the sound head for the production of periodic current pulses for the vibration coil, wherein (a) the permanent magnet of the magnet assembly consists of a permanent magnetic material designated by the formula $$RECo_5$$

wherein
RE represents one of the rare earth elements Y, La, Ce, Pr, Nd, Sm or mixtures thereof, and (b) on at least one of the sound head and the generator-amplifier section there is provided a rapidly releasable device for the mechanical joining of the sound head and generator-amplifier, as well as a means for maintaining the electrical connection between the sound head and generator-amplifier section when the mechanical coupling is released and the sound head is spatially removed from the generator-amplifier section.

2. Speech aid apparatus as claimed in claim 1 wherein a mounting is provided on the sound head for the support of the sound head.

3. Speech aid apparatus as claimed in claim 2 wherein the sound head support is a swiveling support.

4. Speech aid apparatus as claimed in claim 1 wherein the magnet assembly has a first discoidal yoke piece having a core projecting vertically from the plane of the ring, and a second discoidal yoke piece having an opening to accommodate the core of the first yoke piece while leaving an annular gap to receive a guiding sleeve, the said yoke pieces containing between them the permanent magnet which has essentially the same shape as the second pole ring.

5. Speech aid apparatus as claimed in claim 4 wherein the yoke pieces are of a truncoconical configuration on the sides facing away from the permanent magnet.

6. Speech aid apparatus of claim 4 wherein the guiding sleeve is made of plastic.

7. Speech aid apparatus of claim 1 wherein the magnet assembly is mounted in an approximately cylindrical housing section within a recess in the bottom edge thereof, such that the peripheral surface of the magnet system is fitted into the recess and the upper face of the second yoke piece rests against the shoulder of said recess.

8. Speech aid apparatus of claim 7 characterized in that the housing section is made of plastic.

9. Speech aid apparatus of claim 1 wherein the means for maintaining the electrical connection is a connecting cable connected permanently to the sound head at the one end and to the generator-amplifier at the other.

10. Speech aid apparatus of claim 1 wherein the rapidly releasable device for the mechanical joining of the sound head and generator-amplifier is simultaneously constructed as an electrical contact, and an additional electrical contact is produced by the contact of one yoke piece to a spring contact insulatedly disposed on the generator-amplifier section, the means for maintaining the electrical connection being constructed as an adapter cable which can be connected when the mechanical coupling is released.

11. Speech aid apparatus of claim 9 wherein in the upper part of the generator-amplifier section, a storage chamber with a winding device is provided for the connecting cable or adapter cable.

12. Speech aid apparatus of claim 1 wherein the on-off or momentary contact switch is in the form of an actuating means separated from the sound head and generator-amplifier and electrically connected to the generator-amplifier.

13. Speech aid apparatus of claim 12 wherein the on-off or momentary contact switch is in the form of a shallow element having a large actuating surface.

14. Speech aid apparatus of claim 12 wherein the actuating means has devices enabling it to be fastened in the armpit of the laryngectomee.

* * * * *